(12) United States Patent
Zeng

(10) Patent No.: US 11,534,193 B2
(45) Date of Patent: Dec. 27, 2022

(54) PORTABLE MULTIFUNCTIONAL ORAL CAVITY CLEANER

(71) Applicant: Di Zeng, Guangxi (CN)

(72) Inventor: Di Zeng, Guangxi (CN)

( * ) Notice: Subject to any disclaimer, the term of this patent is extended or adjusted under 35 U.S.C. 154(b) by 98 days.

(21) Appl. No.: 17/015,076

(22) Filed: Sep. 8, 2020

(65) Prior Publication Data

US 2020/0397454 A1    Dec. 24, 2020

Related U.S. Application Data

(63) Continuation of application No. PCT/CN2016/107265, filed on Nov. 25, 2016.

(51) Int. Cl.
*A61B 17/24* (2006.01)
*A61C 15/04* (2006.01)
(Continued)

(52) U.S. Cl.
CPC .......... *A61B 17/244* (2013.01); *A61C 15/043* (2013.01); *A61C 17/0202* (2013.01);
(Continued)

(58) Field of Classification Search
CPC ............ A46B 15/0081; A46B 15/0071; A46B 15/0073; A46B 13/04; A46B 13/06;
(Continued)

(56) References Cited

U.S. PATENT DOCUMENTS 1,485,519 A * 3/1924 Nelson ............... A46B 15/0071
132/309
5,947,912 A * 9/1999 Montagnino ........ A61B 17/244
601/142
(Continued)

FOREIGN PATENT DOCUMENTS

CN        2642123 Y     9/2004
CN      201157384 Y    12/2008
(Continued)

OTHER PUBLICATIONS

International search report of PCT Patent Application No. PCT/CN2016/107265 dated Feb. 9, 2017.

*Primary Examiner* — Cris L. Rodriguez
*Assistant Examiner* — Sydney J Pulvidente

(57) ABSTRACT

Disclosed is a portable multifunctional oral cavity cleaner which includes a tongue scraper, a material storage bottle, a material spraying device and a detachable housing; the tongue scraper can be changed into a contracted state from a stretched state via bending, rotating or folding, so as to reduce the volume of the oral cavity cleaner; an oral cavity cleaner body including the tongue scraper in the contracted state is housed in an inner cavity of the housing; and the housing can be reversely combined at the bottom of the oral cavity cleaner after being detached and used as a handle for prolonging the length of the oral cavity cleaner. The present application, featured with small size, light weight and portability, ensures hygiene in the carrying process and realizes multiple functions such as tongue coating removal, oral spray sterilization and interdental cleaning at one time.

10 Claims, 17 Drawing Sheets

(51) Int. Cl.
*A61C 17/02* (2006.01)
*A61C 17/16* (2006.01)
*A61B 17/00* (2006.01)

(52) U.S. Cl.
CPC ...... *A61C 17/16* (2013.01); *A61B 2017/0046* (2013.01); *A61B 2017/00862* (2013.01)

(58) Field of Classification Search
CPC ...... A61B 17/244; A61B 17/24; A45D 44/18; A61C 17/02; A61C 17/0202; A61C 17/0211; A61C 17/024; A61C 17/032; A61C 17/16; A61C 17/22; A61C 17/222; A61C 17/227
USPC ............... 132/322, 329, 309, 311, 308, 200; 401/261–267
See application file for complete search history.

(56) References Cited

U.S. PATENT DOCUMENTS

| | | | | |
|---|---|---|---|---|
| 6,526,991 B2* | 3/2003 | Bodwalk | ............... | A45D 44/18 |
| | | | | 206/581 |
| 2005/0147461 A1* | 7/2005 | Glover | ............... | A46B 11/0072 |
| | | | | 401/278 |

FOREIGN PATENT DOCUMENTS

| | | | | | |
|---|---|---|---|---|---|
| CN | 201337492 Y | 11/2009 | | | |
| CN | 103989533 A | 8/2014 | | | |
| CN | 105125308 A | 12/2015 | | | |
| CN | 204839656 U | 12/2015 | | | |
| CN | 205198176 U | 5/2016 | | | |
| GB | 2357249 A | 6/2001 | | | |
| KR | 20150106554 A | * | 9/2015 | ............ | A46B 5/021 |
| WO | 2015183271 A1 | 12/2015 | | | |
| WO | WO-2015183271 A1 | * | 12/2015 | ........... | A46B 11/001 |

* cited by examiner

PORTABLE MULTIFUNCTIONAL ORAL CAVITY CLEANER

CROSS REFERENCE TO RELATED APPLICATIONS

The present application is a Continuation Application of PCT Application No. PCT/CN2016/107265 filed on Nov. 25, 2016. The contents of the above are hereby incorporated by reference.

BACKGROUND

Field of the Invention

The present application relates to an oral cavity cleaning device, in particular to a portable multifunctional oral cavity cleaner.

Related Arts

Oral cleaning products typically include dental floss, toothpicks, tongue scrapers, cleaning liquid and so on. Currently the multifunctional device that integrates all those products has not appeared on the oral hygiene market. Under the background of prevailing tourism at present, it is inconvenient for people to carry the aforementioned products on the trip. Meanwhile, the existing oral cavity cleaning devices that are not provided with a protective casing are likely to be polluted during carrying. Additionally, the existing kind of tongue scraper that can spray cleaning liquid by squeezing a container bottle has the problems of excess spraying amount of cleaning liquid and poor atomization effect.

CN 201337492 discloses a spray-type tongue scraper which comprises a cleaning head and a cleaning handle, wherein the surface of the cleaning head is provided with cleaning teeth, and the cleaning handle is provided with a groove extending to the cleaning head; an open connecting seat with a cavity is arranged at the tail end of the cleaning handle; a through hole is formed in the connecting seat; the groove is communicated with the cavity through the through hole, and an open end of the connecting seat is connected with a water bottle; cleaning liquid is housed in the water bottle; a bottle plug is arranged on the water bottle; an infusion tube penetrates through the bottle plug and is inserted into the bottom of the water bottle; and the other end of the infusion tube penetrates through the through hole of the connecting seat and is arranged in the groove. The novel tongue scraper is not provided with dental floss or protective casing, and it is inconvenient to carry.

CN 2642123 relates to a structural technology of a toothbrush, including a brush handle and bristles arranged at the front end of the brush handle, wherein the rear part of the brush handle is provided with a groove, and a short rod which can be stored in the groove is hinged at the rear end of the brush handle. According to the application, products such as dental floss, toothpicks and tongue scrapers can be further provided on the short rod. The products can be connected on the brush handle via the above-mentioned hinging mode and stored by folding, thus being convenient to use and not interfering with brushing simultaneously. The toothbrush is multi-purpose, but it is also inconvenient to carry.

SUMMARY

In view of the technical problem, the present application provides a portable multifunctional oral cavity cleaner.

In order to achieve the above object, the present application adopts the following technical solution:

A portable multifunctional oral cavity cleaner includes a tongue scraper and a material storage bottle, and further includes a material spraying device and a detachable housing; the tongue scraper can be changed into a contracted state from a stretched state via a bending, rotating or folding mode; an oral cavity cleaner body including the tongue scraper in the contracted state is housed in an inner cavity of the housing; the housing is detachably connected with the material storage bottle; and the housing can be reversely combined at the bottom of the material storage bottle after being detached.

According to the present application, the oral cavity cleaner body including the tongue scraper in the contracted state is housed in the inner cavity of the housing, thus to avoid being polluted in the carrying process, and the oral cavity cleaner can realize multiple functions such as tongue coating removal, oral spray sterilization and the purpose of convenient carrying. Due to the fact that the tongue scraper can be changed into a contracted state from the stretched state via bending, rotating or folding, the size and volume of the oral cavity cleaner is reduced, making the oral cavity cleaner more compact and portable. The detachable housing is convenient to clean, and after being detached, the housing can be reversely combined at the bottom of the material storage bottle to prolong the whole length of the oral cavity cleaner and used as a handle of the oral cavity cleaner, thus to make the oral cavity cleaner easy to grasp and use; a fluid or powder is stored in the material storage bottle, and the fluid or powder has cleaning and health-care effects; meanwhile, the housing can be reversely combined with the bottom of the material storage bottle to increase the length of the oral cavity cleaner when the oral cavity cleaner is used, and the length of the oral cavity cleaner can be reduced when the oral cavity cleaner body is stored in the housing, thus to make the oral cavity cleaner convenient to carry.

On the basis of the above technical solution, the present application can be further improved and provides more options.

The material spraying device is combined with the material storage bottle, and an outlet of the material spraying device is a spray head arranged on the tongue scraper or a spray head connected near the tongue scraper. The spray head ensures that an oral cavity cleaning agent in the material storage bottle can be completely atomized during use, saving the dosage of the oral cavity cleaning agent.

Further, the tongue scraper can be changed into the contracted state from the stretched state via the bending, rotating or folding mode, comprising: the tongue scraper is an integrated piece made of an elastic material and can be bent into the contracted state; or the tongue scraper is an integrated piece made of an elastic material or a non-elastic material and can be changed into a vertical state from a transversely stretched state via rotating; or the tongue scraper is a multi-piece movable connecting body made of an elastic material or a non-elastic material and can be changed into a folded state from a transversely stretched state via folding.

Further, two ends of the tongue scraper are connected with a push-pull rod, and the tongue scraper can be bent to be contracted or folded to be gathered through the movement of the push-pull rod; or the tongue scraper is connected with one fixed shaft hub or two fixed shaft hubs through a connector, and the tongue scraper can be changed into the vertical state via rotating.

The bending mode of the tongue scraper mentioned here also includes restraining the tongue scraper by the housing when inserting it into the housing.

The material spraying device is a pressing-type material spraying device or a squeezing-type material spraying device; and a pressing plate of the pressing-type material spraying device is arranged on an upper end or an upper side surface of the material storage bottle.

As an embodiment, the housing is formed by combining a protective lid and a shell in a mode comprising a threaded engagement, a snap-fit engagement, or a groove-catch engagement.

The housing is detachably connected with the material storage bottle, preferably with the bottom of the material storage bottle, in a mode comprising a threaded connection, a snap-fit connection, or a groove-catch connection. Preferably, the tongue scraper is provided with a movable material spraying device, which can realize that a fluid or powder can be sprayed out when a switch is turned on and prevented from being sprayed out when the switch is turned off. The movable material spraying device can be provided with a pressing-type switch, which comprises two forms of spraying fluid or powder: the fluid or powder sprays out when a button is pressed, and the fluid or powder stops spraying when the button is released; the fluid or powder sprays out when the button is released, and the fluid or powder stops spraying when the button is pressed. The technical solution can ensure that the fluid or the powder is sprayed only when the switch is turned on and not sprayed when the switch is turned off, so that the fluid or the powder will not leak during carrying, and the dosage of the fluid or the powder can be controlled as required during use.

Preferably, the present application also includes a dual-interface connector. An interface at one end of the connector is connected to a lower part of the material storage bottle, and the housing can be reversely combined at an interface at the other end of the dual-interface connector after being detached, wherein the connection modes include: a threaded connection, a snap-fit connection or a groove-catch connection.

The present application also takes into account different oral cleaning habits and meets the needs of people using dental floss for interdental cleaning. As an embodiment, the present application further includes a dental floss receiving cavity distributed at the bottom of the material storage bottle, and a dental floss cutter is arranged near the dental floss receiving cavity; the dental floss is detachably placed in the dental floss receiving cavity with the dental floss cutter at the bottom of the material storage bottle.

Furthermore, in order to achieve automatic tongue scraping, the present application further includes an electric device arranged for enabling the tongue scraper to automatically vibrate to scrape a tongue. The electric device drives the tongue scraper to vibrate for scraping the tongue, with high frequency, stable amplitude, and a better effect than manual tongue scraping.

Figure 1:
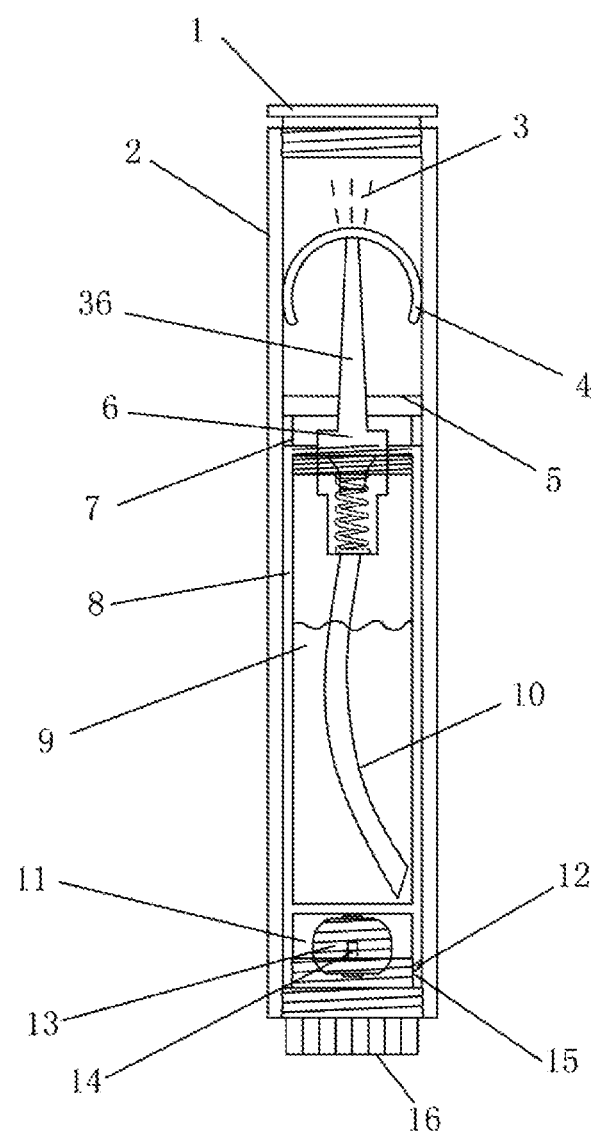
FIG. 1 is a schematic diagram of an overall structure of an embodiment of the present application.
Figure 2:
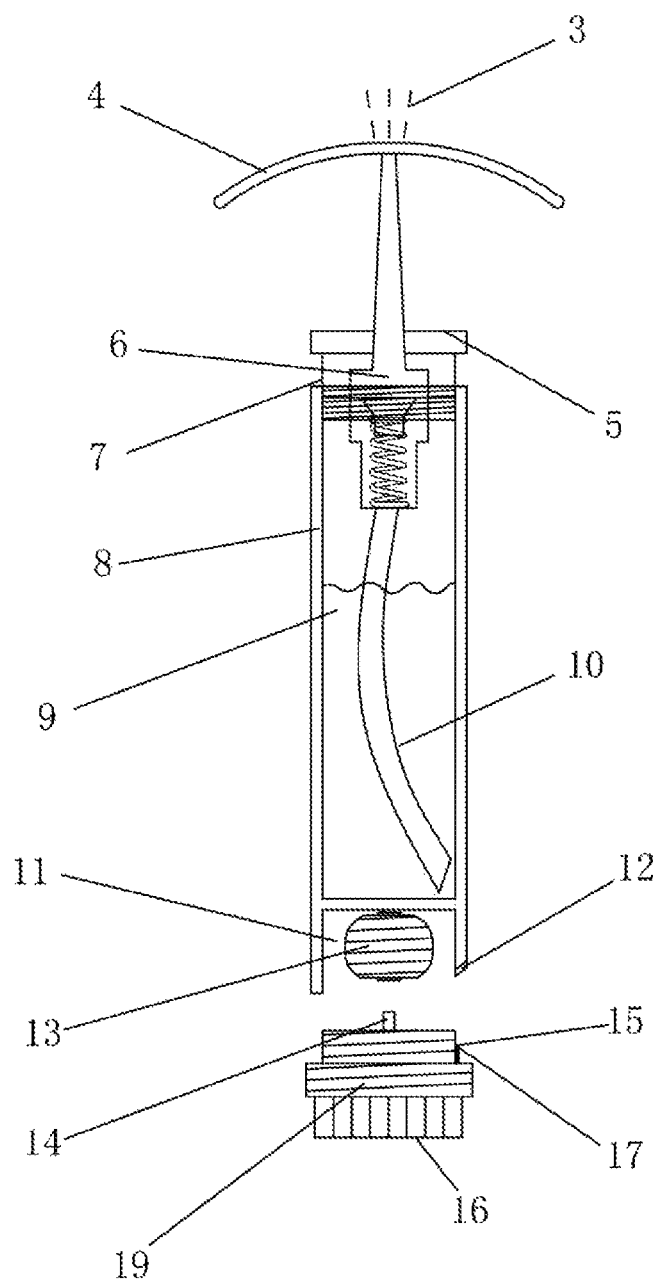
FIG. 2 is a schematic diagram of an internal structure of FIG. 1 with a housing removed, wherein a tongue scraper is in a stretched state.
Figure 3:
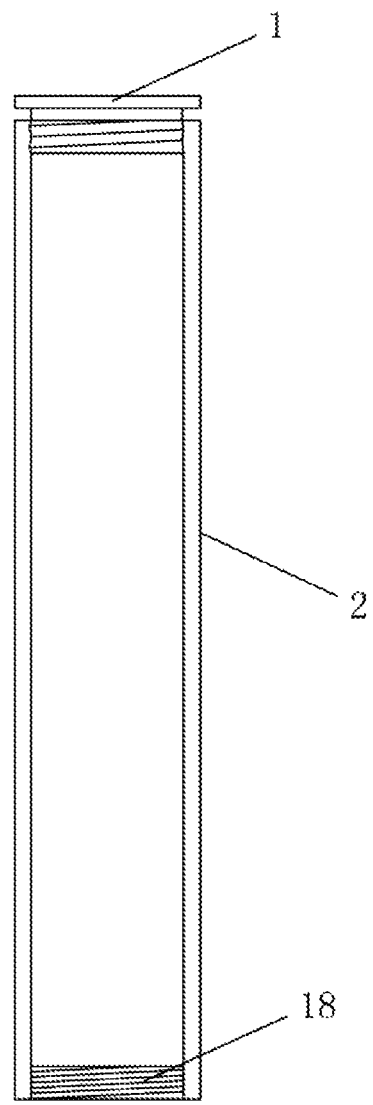
FIG. 3 is a structural schematic diagram of the housing in FIG. 1.
Figure 4:
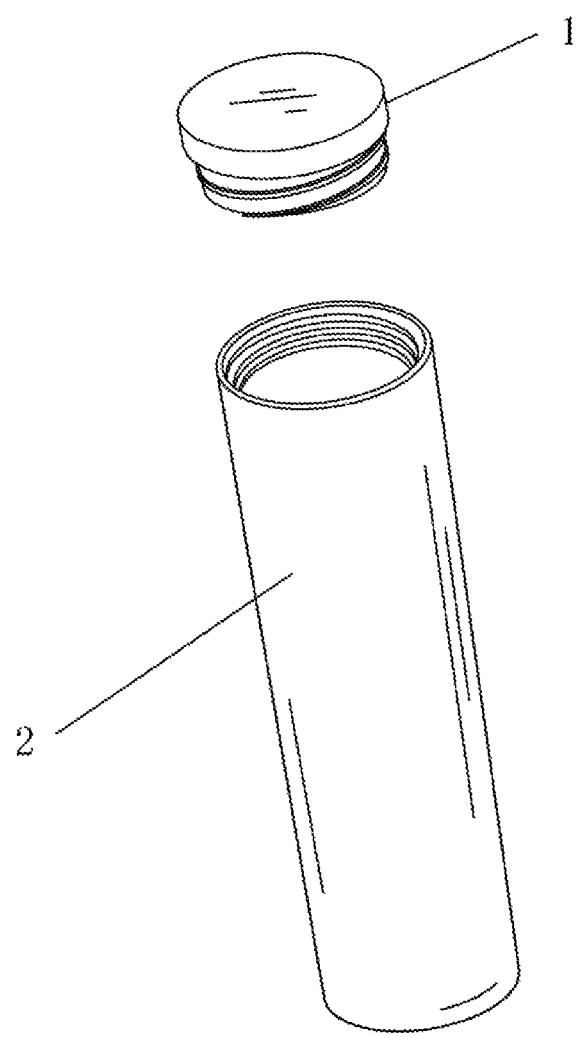
FIG. 4 is an exploded view of the housing shown in FIG. 3.
Figure 5:
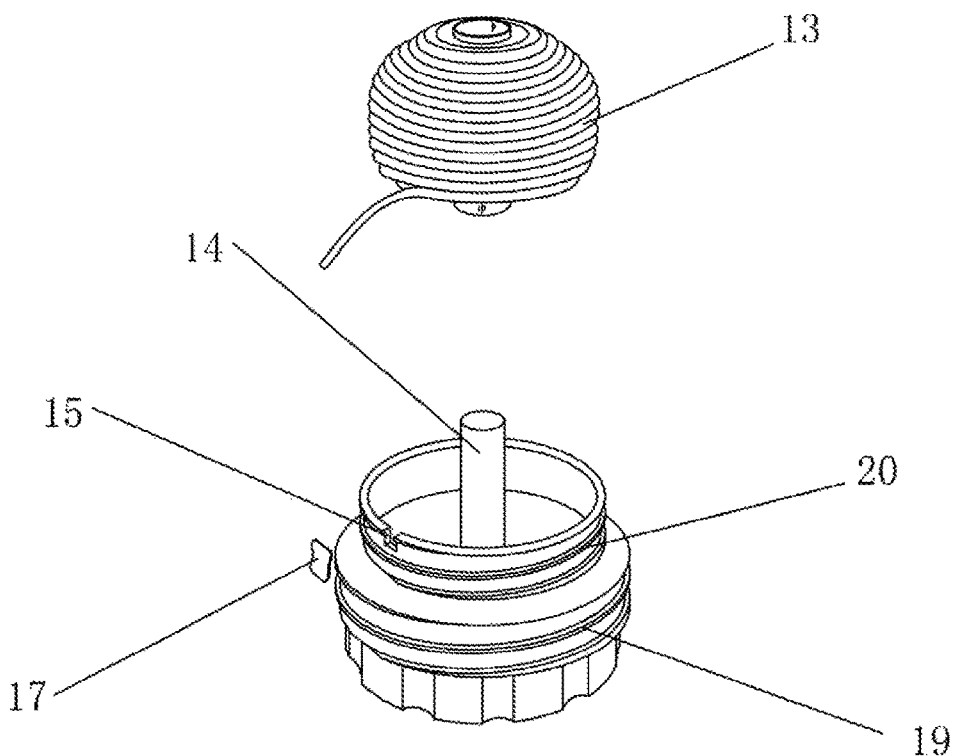
FIG. 5 is an exploded view of the dual-interface connector and dental floss placement configuration at the bottom of FIG. 1.
Figure 6:
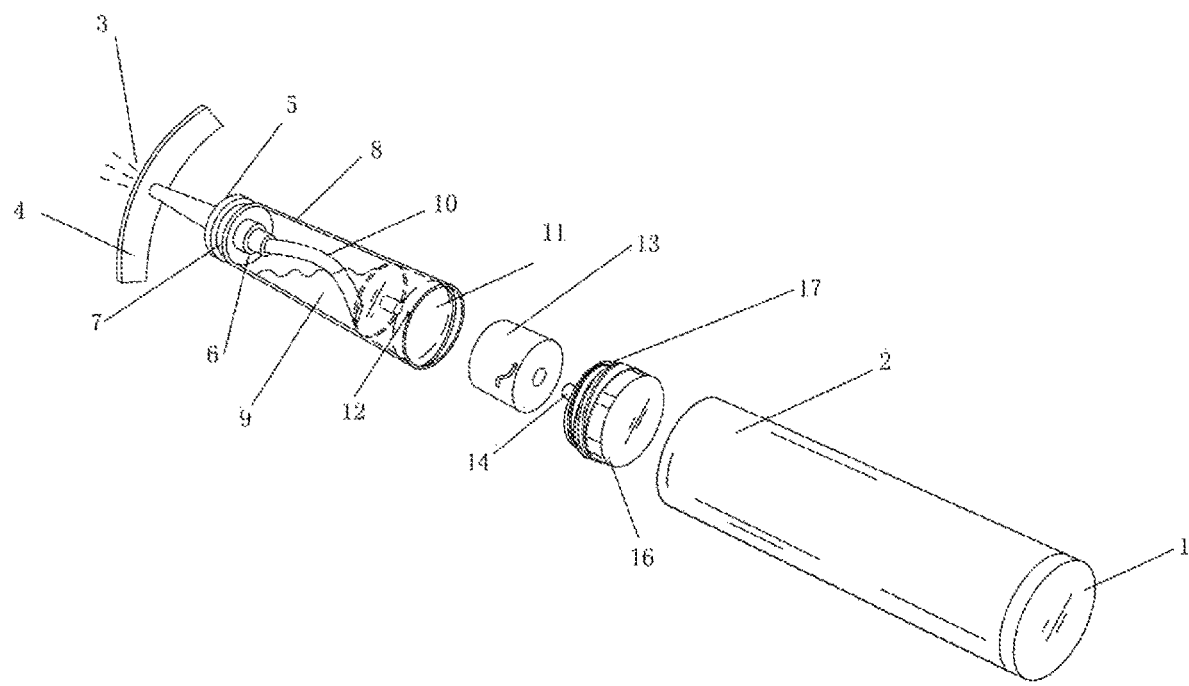
FIG. 6 is an exploded schematic view of the housing of FIG. 1 removed and attached to the bottom of a material storage bottle.

In the drawings, reference numerals used comprise: 1: protective lid; 2: shell; 3: atomizing nozzle; 4: tongue scraper; 5: pressing plate; 6: pressing-type material spraying device; 7: pressing gap; 8: material storage bottle; 9: storage cavity; 10: material conveying conduit; 11: dental floss receiving cavity; 12: dental floss cutter; 13: dental floss; 14: dental floss fixing shaft; 15: dental floss outlet; 16: dual-interface connector; 17: water blocking gasket; 18: internal threads; 19: external threads; 20: fixing ring; 21: movable material spraying device; 22: spray button; 23: vibration switch; 24: motor; 25: charging port; 26: battery; 27: push-pull rod; 28: push-pull slider; 29: upper fixation clamping tooth; 30: lower fixation clamping tooth; 31: foldable tongue scraper; 32: pull rod; 33: shaft I; 34: shaft II; 35: shaft III; 36: external material conveying conduit; 37: partition plate; 38: flat plate tongue scraper; 39: bendable pull rod; and 40: right-angle tongue scraper.

DETAILED DESCRIPTION

The principles and features of the present application will be described below with reference to the accompanying drawings and examples, and the examples cited are only used for explaining the present application, not to limit the scope of the present application.

Example 1

As shown in FIGS. 1-6, the example discloses a portable multifunctional oral cavity cleaner which comprises a tongue scraper 4, a material storage bottle 8, a material spraying device and a detachable housing. Wherein an oral cavity cleaner body including the tongue scraper 4 in a contracted state is housed in an inner cavity of the housing. The bottom of a shell 2 of the housing is provided with internal threads 18, and the shell 2 of the housing is in a threaded connection with the bottom of the material storage bottle 8. The bottom of the material storage bottle 8 is also in a threaded connection with one interface of the dual-interface connector 16, and the shell 2 of the housing can be reversely combined with the other interface of the dual-interface connector 16 at the bottom of the material storage bottle 8 after being detached for prolonging the whole length of the oral cavity cleaner. The housing is formed by combining a protective lid 1 and the shell 2, and the protective lid 1 and the shell 2 are combined in a threaded engagement mode, facilitating mounting and dismounting of the protective lid 1 and the shell 2, and facilitating cleaning of the housing. The tongue scraper 4 is an integrated piece made of an elastic material, and the tongue scraper can be changed into the contracted state from a stretched state via bending, thereby greatly reducing the size and volume of the whole body, and making the whole body more compact and portable. The material spraying device is combined with the material storage bottle 8 through threads. The material spraying device is a pressing-type material spraying device 6, the lower end of which is provided with a material conveying conduit 10, and the upper end of which is provided with an external material conveying conduit 36. The material conveying conduit 10 of the pressing-type material spraying device 6 is arranged in the storage cavity 9 within the material storage bottle 8. An outlet of the material conveying conduit 10 is communicated with the tongue scraper 4 through an external material conveying conduit 36, and is arranged with an atomizing nozzle 3. A pressing plate 5 of the pressing-type material spraying device 6 is arranged on the upper end of a material storage bottle 8. A pressing gap 7 is formed between the pressing plate 5 and the material storage bottle 8. A spring is arranged in the pressing-type material spraying device 6. Fluid or powder in the storage cavity 9 can be sprayed out through the material conveying conduit 10, the external material conveying conduit 36 and the atomizing nozzle 3 by pressing the pressing plate 5. The bottom of the material storage bottle 8 is provided with a dental floss receiving cavity 11 with a dental floss cutter 12. The dental floss receiving cavity 11 is used for storing a replaceable dental floss 13, and the dental floss cutter 12 is used for cutting the dental floss 13. The dual-interface connector 16 is also provided with external threads 19, a fixing ring 20, a dental floss fixing shaft 14, a dental floss outlet 15 corresponding to the dental floss cutter 12, and a water blocking gasket 17 for blocking the dental floss outlet 15. Wherein the dental floss fixing shaft 14 is used for winding the dental floss 13, and the dental floss outlet 15 is positioned on the fixing ring 20, so that the dental floss 13 can be pulled out. The water blocking gasket 17 can block the dental floss outlet 15 to avoid contamination of the dental floss 13 during cleaning, and the external threads 19 can cooperate with the internal threads 18 on the shell 2 to enable connection of the housing to the dual-interface connector 16.

Example 2

Figure 7:
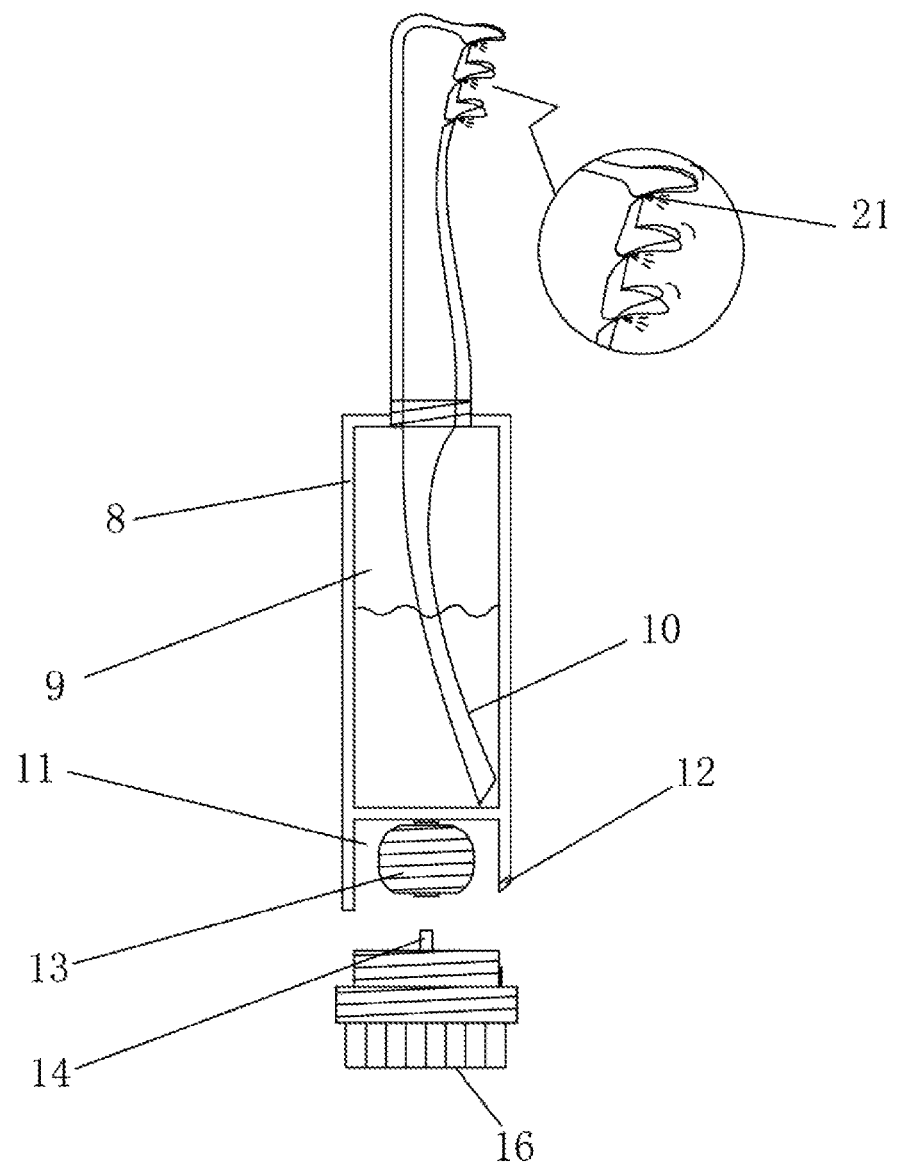
FIG. 7 is a schematic diagram of an overall (with the housing removed) structure of an embodiment where the tongue scraper is provided with a movable material spraying device; wherein the number of the tongue scraper is three, and the upper right corner is an enlarged schematic diagram of the movable material spraying device.

As shown in FIG. 7, the example discloses a portable multifunctional oral cavity cleaner. Different from the example 1, the tongue scraper 4 is provided with a movable material spraying device 21, and the number of the tongue scrapers in FIG. 7 is 3. The movable material spraying device 21 is provided with a pressing-type switch, and liquid or powder is sprayed out when a button is pressed and prevented from being sprayed out when the button is released. The pressing-type switch could also be configured in the form that the fluid or powder is sprayed out when the button is released and prevented from being sprayed out when the button is pressed. This example can ensure that the fluid or powder is sprayed out only when the switch is turned on and is not sprayed out when the switch is turned off. Thus there is no fluid leakage or powder leakage during carrying and the spraying amount of the fluid or powder can be controlled as required during use.

Example 3

Figure 8:
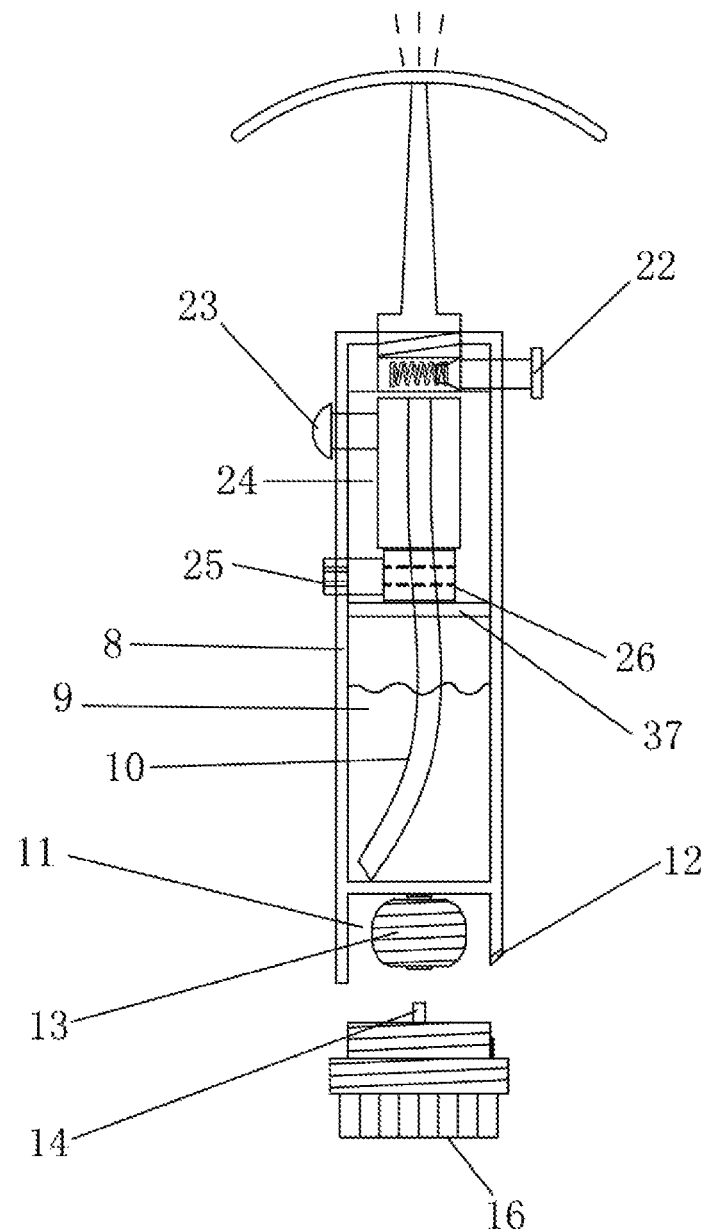
FIG. 8 is a schematic diagram of an overall (with the housing removed) structure of an embodiment provided with an electrically powered device.

As shown in FIG. 8, the present example discloses a portable multifunctional oral cavity cleaner. Different from the example 1, a spray button 22 of a material spraying device is provided on the top side of the material storage bottle 8, and spraying of fluid or powder can be achieved by pressing the spray button 22. The example further comprises an electric device for enabling the tongue scraper to automatically vibrate to scrape a tongue. A transverse partition plate 37 is arranged inside the material storage bottle 8, by which the storage cavity 9 is separated from an electric device, and the material conveying conduit 10 is communicated with the storage cavity 9 through the partition plate 37; the electric device is provided on the partition plate 37 and comprises a vibration switch 23, a motor 24, a charging port 25 and a battery 26, wherein the motor 24 is located on the upper part of the material storage bottle 8; the vibration switch 23 is arranged on the side of the motor and passes through the material storage bottle 8; the battery 26 is located below the motor 24, and the charging port 25 is located on the side of the battery 26 and passes through the material storage bottle 8. The electric device drives the tongue scraper to vibrate for scraping the tongue, with high frequency, stable amplitude, and a better effect than manual tongue scraping.

Example 4

Figure 9:
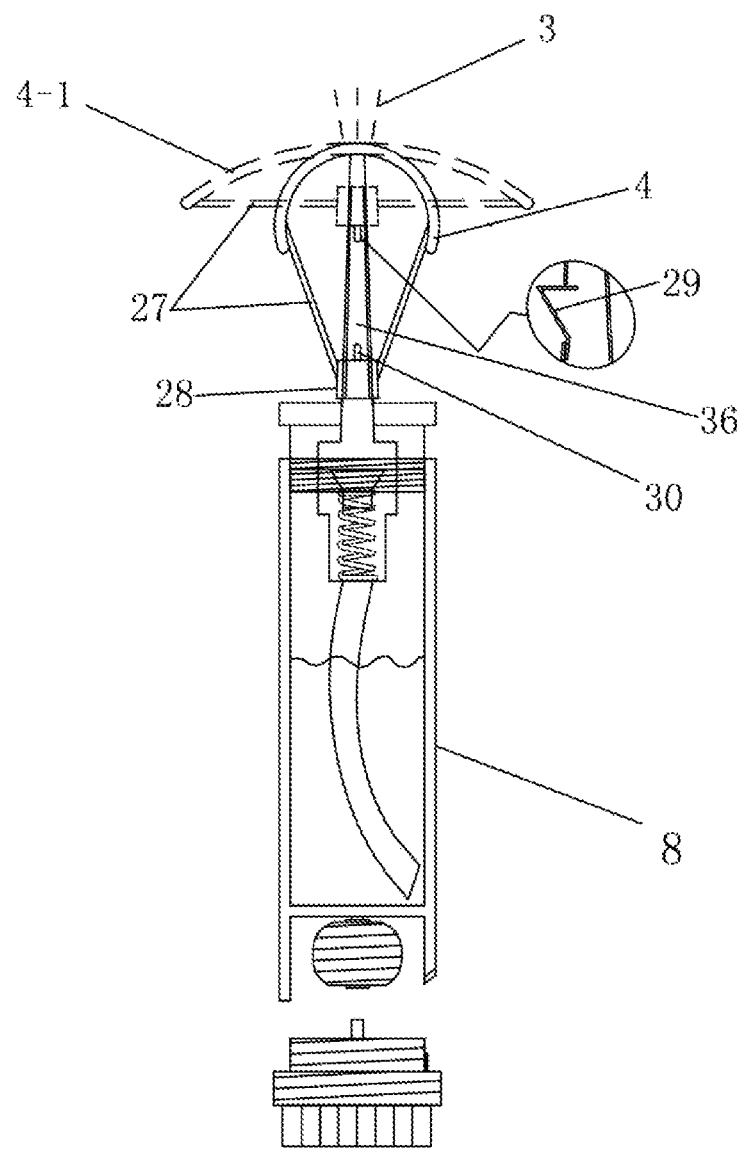
FIG. 9 is a schematic diagram showing an overall structure (with the housing removed) of an embodiment in which both ends of the tongue scraper are connected to a push-pull rod; wherein the middle part of the right side in the drawing is an enlarged schematic diagram of an upper fixation clamping tooth.
Figure 10:
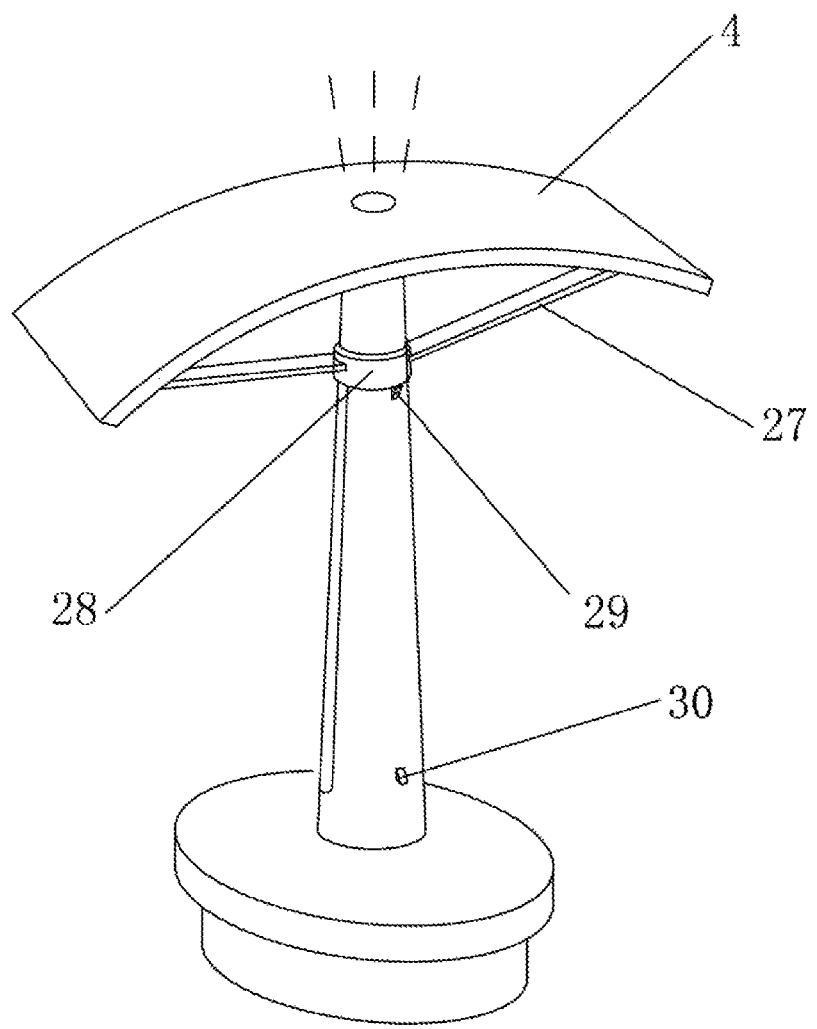
FIG. 10 is a schematic diagram of the tongue scraper of FIG. 9 in a stretched state.
Figure 11:
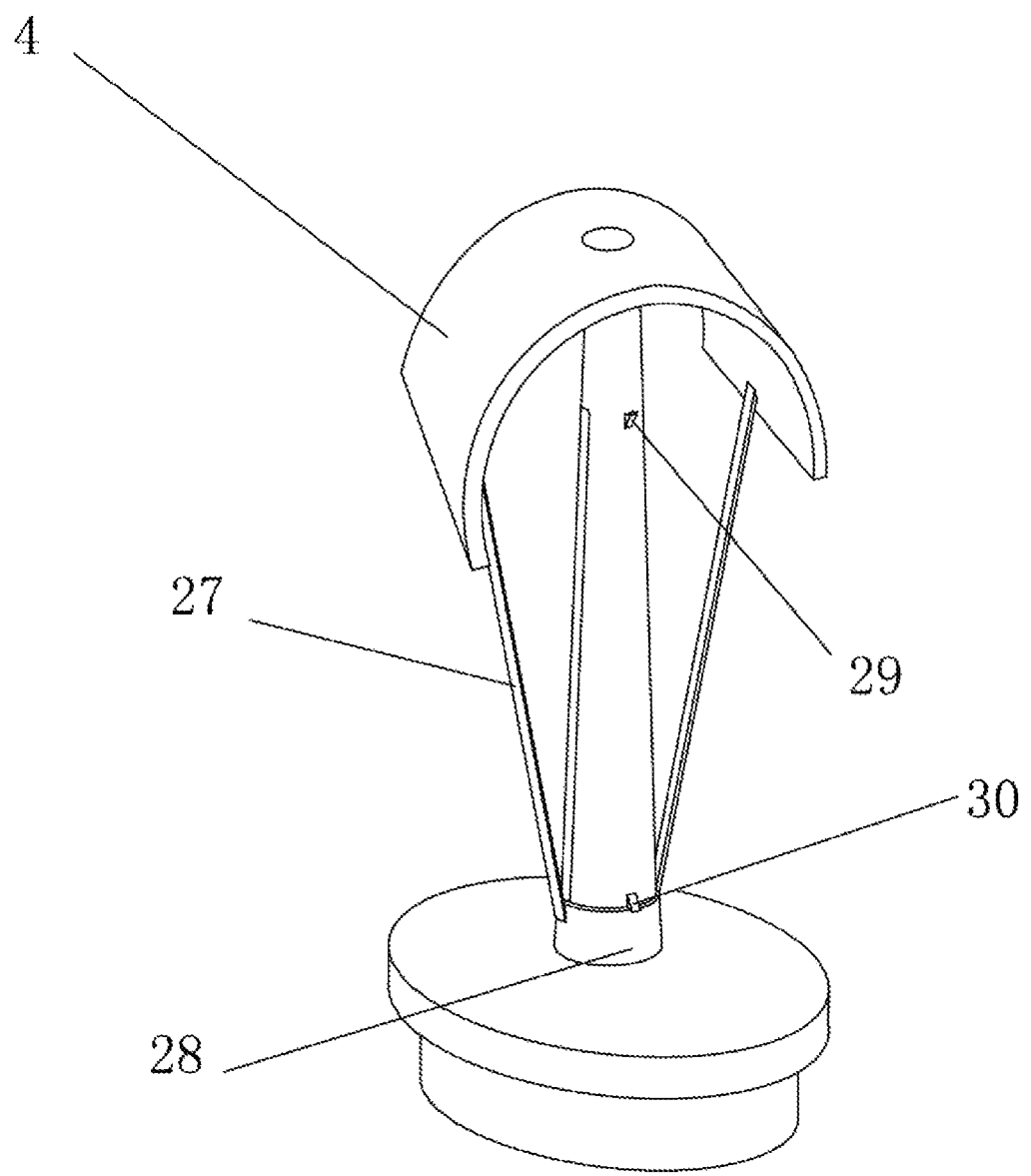
FIG. 11 is a schematic diagram of the tongue scraper of FIG. 9 in a contracted state.

As shown in FIGS. 9-11, the example discloses a portable multifunctional oral cavity cleaner, which is different from the example 1 in that a slidable push-pull slider 28, an upper fixation clamping tooth 29 and a lower fixation clamping tooth 30 are arranged on the external material conveying conduit 36, and the upper fixation clamping tooth 29 and the lower fixation clamping tooth 30 are respectively arranged on the upper part and the lower part of the external material conveying conduit 36 and can clamp the push-pull slider 28; the two ends of the tongue scraper 4 are connected with a push-pull slider 28 through a push-pull rod 27, and the push-pull slider 28 can slide up and down along the external material conveying conduit 36. When the push-pull slider 28 slides up and down, the tongue scraper 4 can be stretched and contracted; when the push-pull slider 28 is positioned above the upper fixation clamping tooth 29, the tongue scraper 4 (the tongue scraper 4-1) is in a stretched state as shown in the tongue scraper 4-1 in the dotted line part of FIG. 9 and the tongue scraper 4 in FIG. 10; and when the push-pull slider 28 is positioned below the lower fixation clamping tooth 30, the tongue scraper 4 is in the contracted state, as shown in the tongue scraper 4 in the solid line part of FIG. 9 and the tongue scraper 4 in FIG. 11.

Example 5

Figure 12:
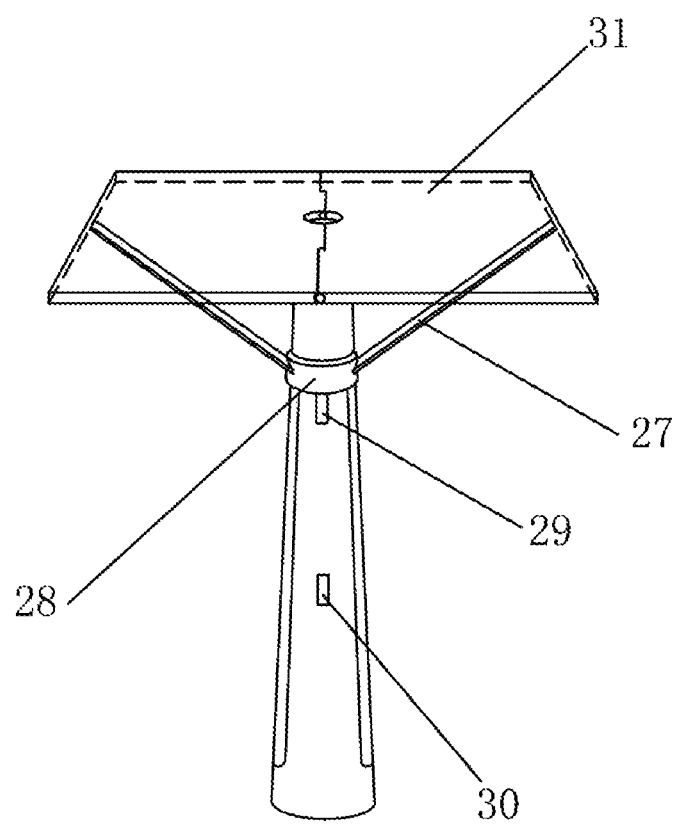
FIG. 12 is a schematic diagram showing an overall (with the housing removed) structure of an embodiment in which the tongue scraper is a two-piece movable connecting body and both ends are connected to a push-pull rod.
Figure 13:
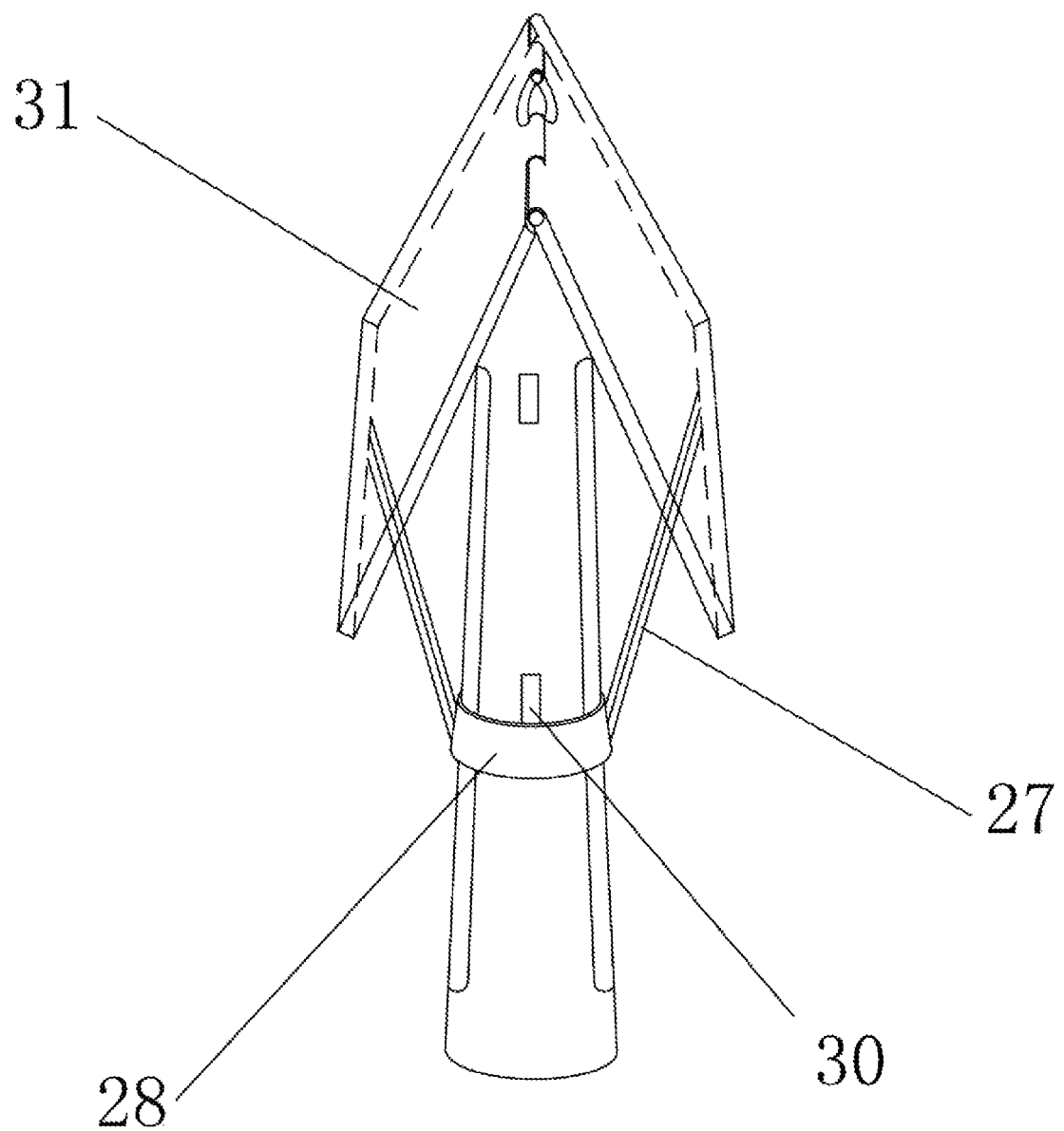
FIG. 13 is a schematic diagram of the tongue scraper of FIG. 12 in a contracted state.

As shown in FIGS. 12-13, the example discloses a portable multifunctional oral cavity cleaner, which is different from the example 4 in that, the tongue scraper is a foldable tongue scraper 31, and the two movable connecting bodies are changed from a transversely stretched state to a folded state by folding in a manner including, but not limited to, hinging. As shown in FIG. 12, when the push-pull slider 28 is positioned above the upper fixation clamping tooth 29, the foldable tongue scraper 31 can be in the stretched state; as shown in FIG. 13, and when the push-pull slider 28 is positioned below the lower fixation clamping tooth 30, the foldable tongue scraper 31 is in the folded state.

Example 6

Figure 14:
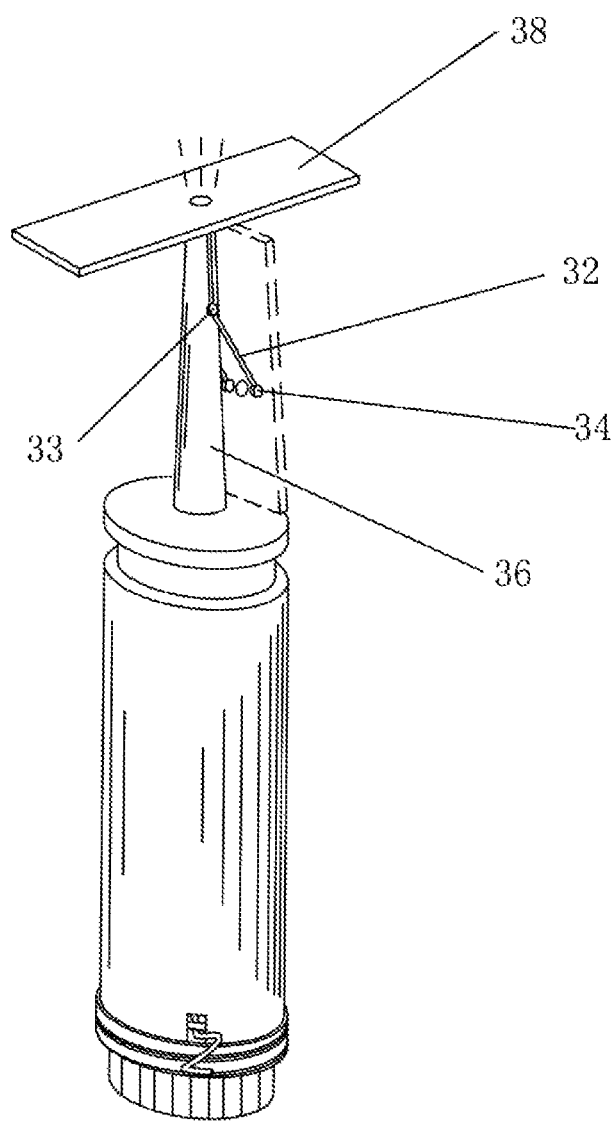
FIG. 14 is a structural view of an embodiment in which a tongue scraper is attached to two fixed shaft hubs by a coupling member, wherein the coupling member is a rigid body.

As shown in FIG. 14, the example discloses a portable multifunctional oral cavity cleaner, which is different from the example 1 in that the tongue scraper is a flat plate tongue scraper 38. A shaft I 33 is arranged on the external material conveying conduit 36, a shaft II 34 is arranged on the flat plate tongue scraper 38, and the shaft I 33 is connected with the shaft II 34 through a pull rod 32. The flat plate tongue scraper 38 is not fixed with the external material conveying conduit 36, and the pull rod 32 can rotate along the shaft I 33. When the shaft II 34 rotates to the uppermost end, as shown by solid lines in FIG. 14, the flat plate tongue scraper 38 is in a stretched state, and when the shaft II 34 is rotated to the lowermost end, as shown in dotted lines in FIG. 14, the flat plate tongue scraper 38 is in a folded state. Also different from example 1, the portable multifunctional oral cavity cleaner is not provided with a water blocking gasket.

Example 7

Figure 15:
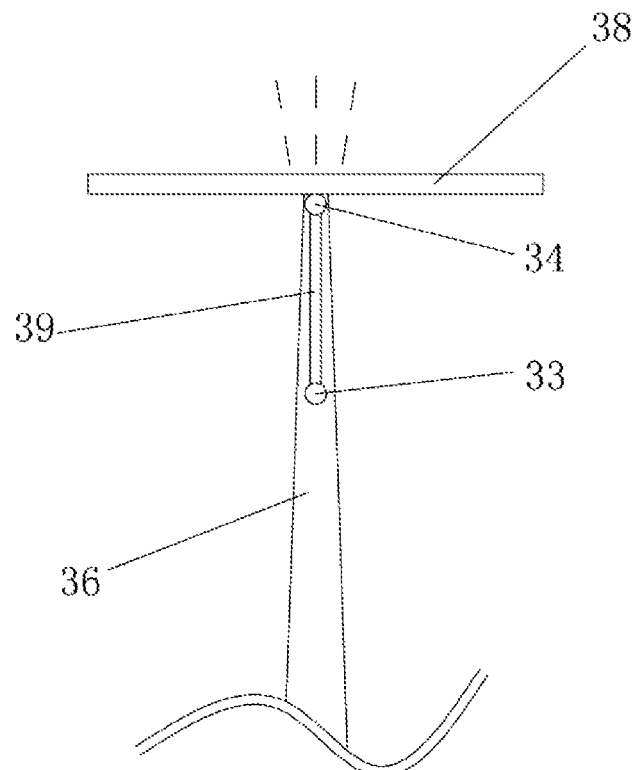
FIG. 15 is a structural view of an embodiment in which a tongue scraper is attached to two fixed shaft hubs by a coupling member, wherein the coupling member is foldable.
Figure 16:
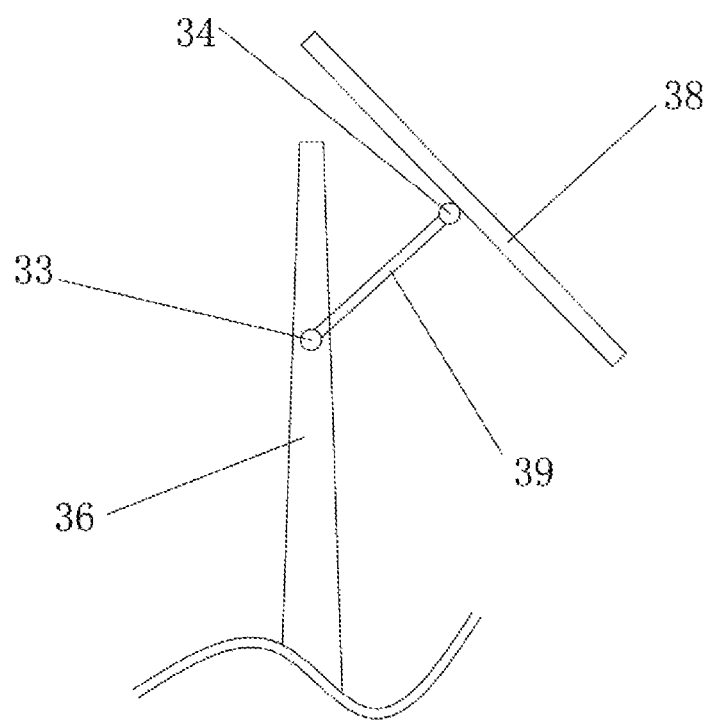
FIG. 16 is a process state view of FIG. 15.
Figure 17:
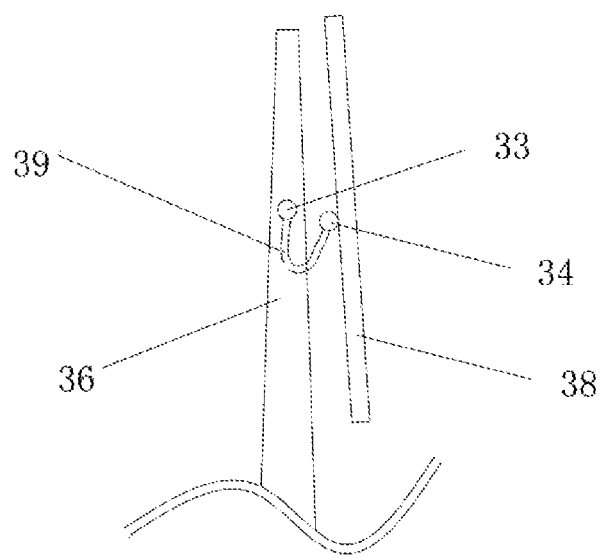
FIG. 17 is a contracted state view of FIG. 15.

As shown in FIGS. 15-17, the example discloses a portable multifunctional oral cavity cleaner, which is different from the example 6 in that, the pull rod is a bendable pull rod 39. FIGS. 15-17 show the process from a stretched state to a folded state of the flat plate tongue scraper 38, wherein the bendable pull rod 39 can be bent as shown in FIG. 17, realizing the position adjustment of the flat plate tongue scraper 38 in the folded state.

Example 8

Figure 18:
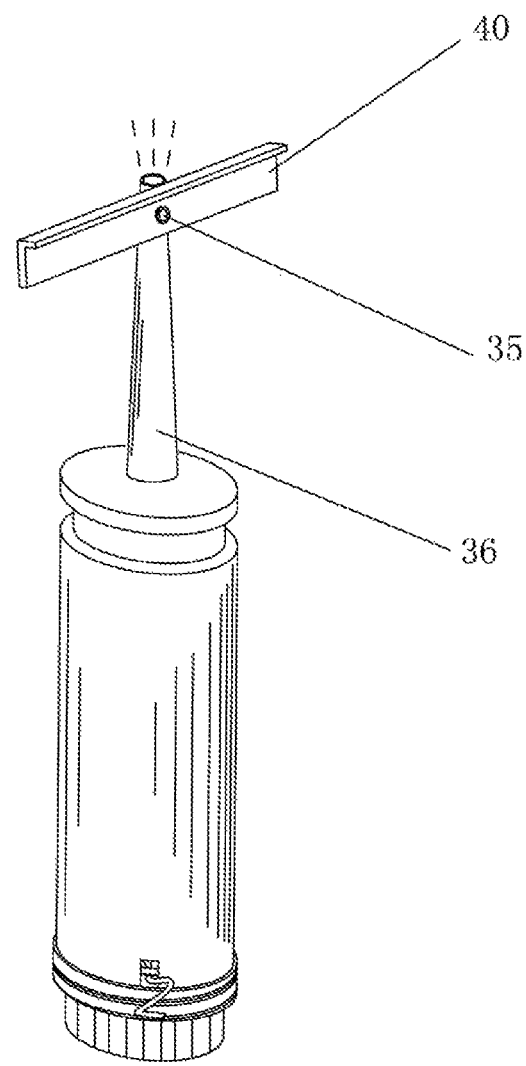
FIG. 18 is a structural view of an embodiment of a tongue scraper attached to a fixed shaft hub.
Figure 19:
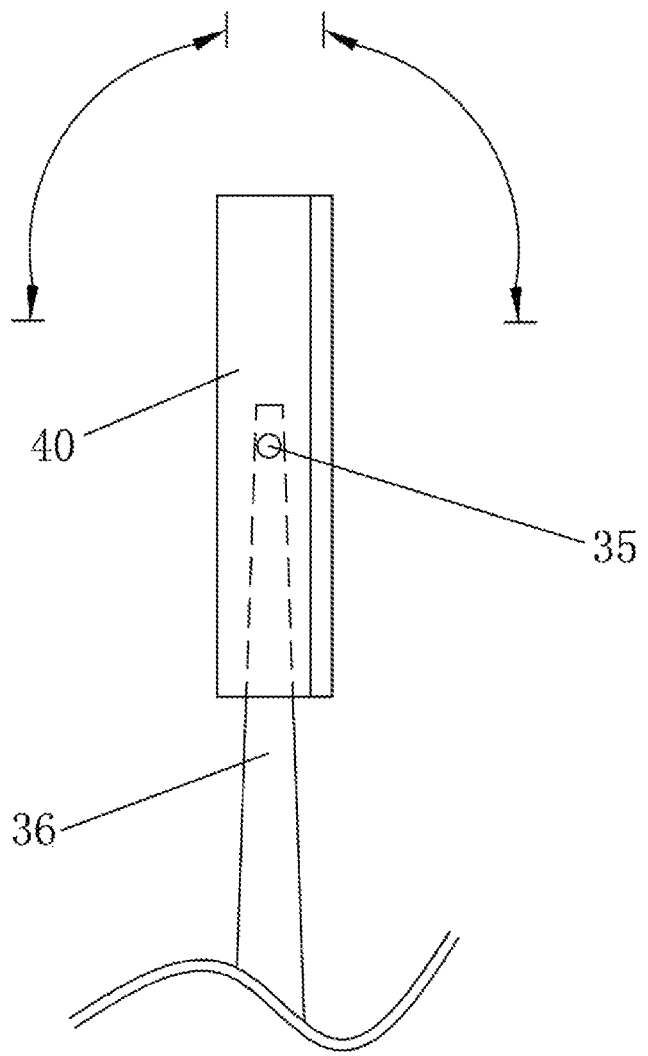
FIG. 19 is a contracted state view of FIG. 18.

As shown in FIGS. 18 to 19, the example discloses a portable multifunctional oral cavity cleaner, which is different from the example 1 in that, the tongue scraper is a right-angle tongue scraper 40, and the right-angle tongue scraper 40 is arranged on the side of the top of the external material conveying conduit 36 through a shaft III 35. The right-angle tongue scraper 40 can rotate around the shaft III 35, and when the right-angle tongue scraper 40 is perpendicular to the external material conveying conduit 36, the right-angle tongue scraper 40 is in a stretched state as shown in FIG. 18; when the right-angle tongue scraper 40 is parallel to the external material conveying conduit 36, the right-angle tongue scraper 40 is in the folded state, as shown in FIG. 19. Also different from example 1, the portable multifunctional oral cavity cleaner is not provided with a water blocking gasket.

While the present application has been particularly shown and described with reference to preferred embodiments thereof, it will be understood by those skilled in the art that various changes in form and details may be made therein without departing from the spirit and scope of the present application, and such modifications and variations all fall in the protection extent of the claims of the present disclosure.

What is claimed is:

1. A portable multifunctional oral cavity cleaner, comprising a tongue scraper and a material storage bottle, wherein
the oral cavity cleaner further comprises a material spraying device and a detachable housing; the tongue scraper is a multi-piece movable connecting body made of an elastic material or a non-elastic material, and can be changed into a folded state from a transversely stretched state via folding; an oral cavity cleaner body comprising the tongue scraper in the folded state is housed in an inner cavity of the housing; the housing is detachably connected with the material storage bottle; and the housing can be reversely combined at the bottom of the material storage bottle after being detached; the material spraying device is combined with the material storage bottle;
wherein the oral cavity cleaner further comprises a dental floss receiving cavity, wherein the dental floss receiving cavity is distributed at the bottom of the material storage bottle, and a dental floss cutter is further arranged near the dental floss receiving cavity.

2. The oral cavity cleaner of claim 1, wherein
two ends of the tongue scraper are connected with a push-pull rod, and the tongue scraper can be bent to be contracted or folded to be gathered through the movement of the push-pull rod.

3. The oral cavity cleaner of claim 1, wherein the material spraying device is a pressing-type material spraying device; and a pressing plate of the pressing-type material spraying device is arranged on an upper end or an upper side surface of the material storage bottle.

4. The oral cavity cleaner of claim 1, wherein the housing is formed by combining a protective lid and a shell in a mode comprising a threaded engagement, a snap-fit engagement, or a groove-catch engagement.

5. The oral cavity cleaner of claim 1, wherein the housing is detachably connected with the material storage bottle in a mode comprising a threaded connection, a snap-fit connection, or a groove-catch connection.

6. The oral cavity cleaner of claim 1, wherein the tongue scraper is provided with a movable material spraying device, so that a fluid or powder can be sprayed out when a switch is turned on and prevented from being sprayed out when the switch is turned off.

7. The oral cavity cleaner of claim 1, wherein the oral cavity cleaner further comprises a dual-interface connector, an interface at one end of the dual-interface connector is connected to a lower part of the material storage bottle, and the housing can be reversely combined at an interface at the other end of the dual-interface connector after being detached.

8. The oral cavity cleaner of claim 1, wherein the oral cavity cleaner further comprises an electric device arranged for enabling the tongue scraper to automatically vibrate to scrape a tongue.

9. A portable multifunctional oral cavity cleaner, comprising a tongue scraper and a material storage bottle, wherein the oral cavity cleaner further comprises a material spraying device and a detachable housing; the tongue scraper is a multi-piece movable connecting body made of an elastic material or a non-elastic material, and can be changed into a folded state from a transversely stretched state via folding; an oral cavity cleaner body comprising the tongue scraper in the folded state is housed in an inner cavity of the housing; the housing is detachably connected with the material storage bottle; and the housing can be reversely combined at the bottom of the material storage bottle after being detached; the material spraying device is combined with the material storage bottle; wherein the tongue scraper is provided with a movable material spraying device, so that a fluid or powder can be sprayed out when a switch is turned on and prevented from being sprayed out when the switch is turned off.

10. A portable multifunctional oral cavity cleaner, comprising a tongue scraper and a material storage bottle, wherein the oral cavity cleaner further comprises a material spraying device and a detachable housing; the tongue scraper is a multi-piece movable connecting body made of an elastic material or a non-elastic material, and can be changed into a folded state from a transversely stretched state via folding; an oral cavity cleaner body comprising the tongue scraper in the folded state is housed in an inner cavity of the housing; the housing is detachably connected with the material storage bottle; and the housing can be reversely combined at the bottom of the material storage bottle after being detached; the material spraying device is combined with the material storage bottle; wherein the oral cavity cleaner further comprises an electric device arranged for enabling the tongue scraper to automatically vibrate to scrape a tongue.

* * * * *